US007005139B2

(12) United States Patent
Wong et al.

(10) Patent No.: US 7,005,139 B2
(45) Date of Patent: Feb. 28, 2006

(54) COMPOSITIONS AND METHODS FOR THE TARGETED DELIVERY OF AGENTS TO TREAT LIVER CANCER

(75) Inventors: Jeffrey Tze Fei Wong, Mid-levels (HK); Shui Ying Tsang, Shatin (HK)

(73) Assignee: Hong Kong University of Science and Technology, Kowloon (HK)

( * ) Notice: Subject to any disclaimer, the term of this patent is extended or adjusted under 35 U.S.C. 154(b) by 27 days.

(21) Appl. No.: 09/827,255

(22) Filed: Apr. 5, 2001

(65) Prior Publication Data

US 2002/0146449 A1    Oct. 10, 2002

(51) Int. Cl.
A61K 9/127    (2006.01)
A61K 48/00    (2006.01)
A61K 38/00    (2006.01)

(52) U.S. Cl. .............................. 424/450; 514/44; 514/2

(58) Field of Classification Search .................... 435/6, 435/7.23, 7.5, 325, 354, 366, 375; 514/2, 514/44; 530/300, 350; 536/23.1, 24.5; 424/450
See application file for complete search history.

(56) References Cited

OTHER PUBLICATIONS

Lawrence D. Mayer et al., Designing Liposomal anticancer drug formulations for specific therapeutic applications, Journal of Liposome Research, 10 (2 &3), pp. 99-115, 2000.*
Francis J. Martin, Future Prospects for Stealth Liposomes in Cancer Therapy, pp. 3-8.*
Daniel E. Lopes de Menezes et al., Molecular and Pharmacokinetic Properties Associated with the Therapeutics of Bcl-2 Antisense Oligonucleotide G3139 Combined with Free and Liposomal Doxorubicin, Clinical Cancer Research. vol. 6, pp. 2891-2902, Jul. 2000.*
G. Pratt et al., Liposomal Daunorubicin: In Vitro And In Vivo Efficacy In Multiple Myeloma, Hematological Oncology, 16, pp. 47-55, 1998.*
Roman Perez-Soler et al., Anthracycline Antibiotics with High Liposome entrapment: Structural Features and Biological Activity, Cancer Research 50, pp. 4260-4266, 1990.*
Jung-Hyun Park et al., Detection of the Asialoglycoprotein Receptor on Cell Lines of Extrahepatic Origin, Biochemical and Biophysical Research Communications, 244, pp. 304-311, 1998.*
V. Neitchev et al., Kinetic and Role of x1—Acid Glycoprotein-dependent Osmotic Transport of Water and Ions in Palmitoyl-L-oleoyl Phophatidylcholine Liposomes, Int. J. Biochem. Cell Biol. vol. 29, No. 4, pp. 689-701, 1997.*
G.N. Hortobagyi, Anthracyclines in the Treatment of Cancer, Drugs 1997; 54 SUPPL. 4, pp. 1-7.*
Allen et al, Advanced Drug Delivery Reviews 21 (1996): 117-133.*
AD Branch, TIBS, "A good antisense molecule is hard to find," Feb. 1998, pp. 45-50.*
DW Green et al., American College of Surgeons,"Antisenes Oligonucleotides: An Evolving Technology for the Modulation of Gene Expression in Human Disease," Jul. 2000,vol. 191, No.1, pp. 93-105.*
K-Y Jen et al., Stem Cells, "Suppression of Gene Expression by Targeted Disruption of Messenger RNA: Available Options and Current Strategies," 2000, 18; pp. 307-319.*
WM Flanagan et al., Research, "Cellular penetration and antisense activity by a phenoxazine-substituted heptanucleotide," Oct. 1998, pp. 1-5.*
S Agrawal et al., Molecular Medicine Today," Antisense therapeutics: is it as simple as complementary base recognition?" Feb. 2000, vol. 6, pp. 1-10.*
H Fritz et al., Journal of Colloid and Interface Science," Cationic Polystyrene Nanoparticles: Preparation and Characterization of a Model Drug Carrier System for Antisense Oligonucleotides," 1997, 195, pp. 272-288.*
DDF Ma et al., Biotechnology Annual Review," Synthetic oligonucleotides as therapeutics: the coming of age,"Jun. 2000, vol. 5, pp. 155-196.*
CF Bennett et al., Methods in Molecular Medicine: Antisense Therapeutics," Pharmacology of Antisense Therapeutic Agents," 1996, pp. 13-46.*

* cited by examiner

Primary Examiner—James Schultz
(74) Attorney, Agent, or Firm—Baker & McKenzie LLP

(57) ABSTRACT

The invention provides compositions containing an effective amount of a therapeutic agent encapsulated in a liposome coupled to a desialyated glycoprotein, e.g., desialyated glycoprotein-α1. This invention further provides methods for the targeted delivery of a therapeutic agent to a tissue expressing asialoglycoprotein receptors by delivery to the tissue an effective amount of a composition containing an effective amount of the agent encapsulated in a liposome coupled to a desialyated glycoprotein, e.g., desialyated glycoprotein-α1. Also provided by this invention is a method for inhibiting the proliferation of liver cancer by administering to a subject in need of such therapy an effective amount of a composition containing doxorubicin encapsulated in desialyated glycoprotein-α1 coupled to a liposome.

11 Claims, 7 Drawing Sheets

COMPOSITIONS AND METHODS FOR THE TARGETED DELIVERY OF AGENTS TO TREAT LIVER CANCER

TECHNICAL FIELD

The present invention relates to the field of drug delivery, pharmacology and cancer chemotherapy.

BACKGROUND

Throughout this disclosure, various publications are referenced by a number within parenthesis. The full bibliographic citation for each reference can be found at the end of this application, immediately preceding the claims. The disclosures of these references are hereby incorporated by reference into this disclosure to more fully describe the state of the art to which this invention pertains.

Most of the cytotoxic drugs used in cancer chemotherapy have a narrow chemotherapeutic utility and serious side effects at high dosages. As a result, drug delivery systems have been developed to modify the biodistribution of cytotoxic drugs, improving their selectivity for tumors or reducing the damage to normal tissues. Liposomes have been used extensively in this regard. The use of liposomes as a drug delivery system has provided a means to improve the therapeutic utility of some conventional drugs [7, 19]. Since many liposomes are rapidly taken up by the cells of the mononuclear phagocyte system or reticuloendothelial system (RES) [12, 20], they have been effective in delivering drugs to organs of the RES. However, their rapid clearance from the bloodstream has also limited their utility for transporting drugs to disease sites beside the RES.

Recently prolongation of the circulation of liposomes in blood and reduction of its uptake by RES have been achieved when the liposomes are stabilized by a polyethylene glycol head group [12, 21]. The increased circulation titers have made possible enhanced antitumor activity [7]. Another approach has been to modify the liposomes to attain active targeting to tumor cells by conjugating the liposomes with antibodies specific for tumor cells [11,22]. One potential problem with antibody-coated liposomes is that they may be more immunogenic, resulting in shorter circulatory half-life, obviously multiple considerations need to be made in designing liposomes as a drug delivery system.

Accordingly, a need exists to provide compositions and methods for tissuespecific delivery of drugs and in particular, for drugs specific for malignant liver tissue. This invention satisfies these needs and provides related advantages as well.

DISCLOSURE OF THE INVENTION

The invention provides compositions containing an effective amount of a therapeutic agent encapsulated in a liposome coupled to a desialyated glycoprotein, e.g., desialyated glycoprotein-α1.

This invention further provides methods for the targeted delivery of a therapeutic agent to a tissue expressing asialoglycoprotein receptors by delivery to the tissue an effective amount of a composition containing an effective amount of the agent encapsulated in a liposome coupled to a desialyated glycoprotein, e.g., desialyated glycoprotein-α1.

Also provided by this invention is a method for inhibiting the proliferation of liver cancer by administering to a subject in need of such therapy an effective amount of a composition containing doxorubicin encapsulated in desialyated glycoprotein-α1 coupled to a liposome.

DISCLOSURE OF THE INVENTION

Figure 1:
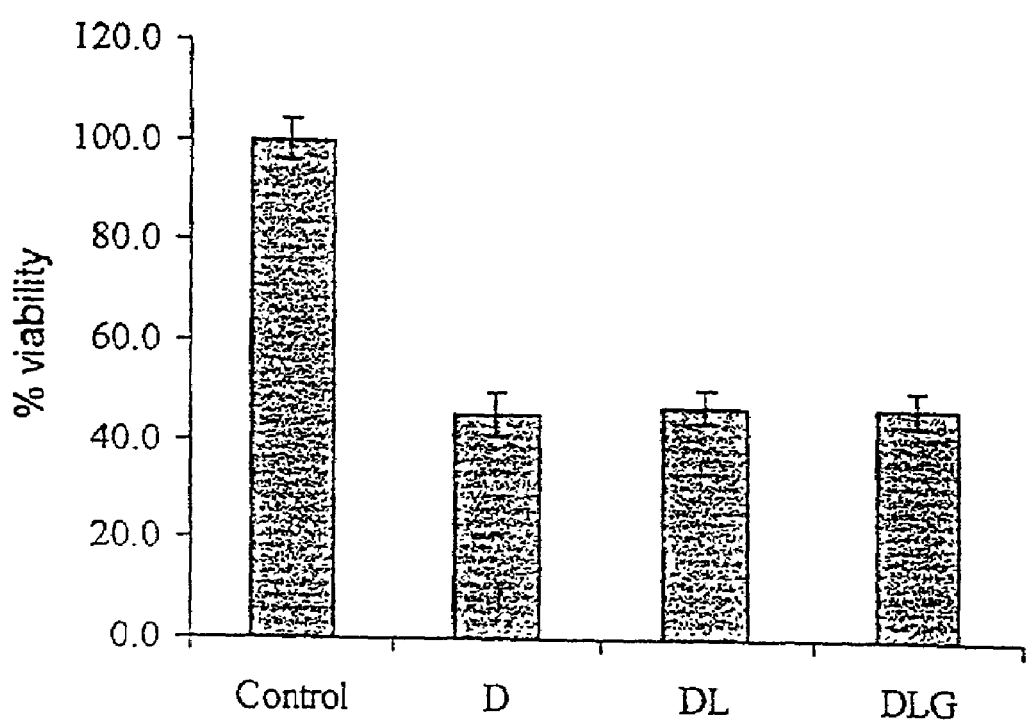
FIG. 1 shows doxorubicin-induced cytotoxicity in hepatoma cells. HepG2 cells were incubated with 5 μM equivalents of D, DL or DLG for 24 h at 37° C. Cytotoxicity was measured using the standard MTT assay. Each column represents the mean ±s.d. (n=8).

It is an object of this invention to provide a liver-targeting delivery system of liposomal encapsulated therapeutic agents for use in cancer therapy. In particular, it is an object of this invention to provide liposomal doxorubicin for use in cancer chemotherapy.

It is an object of this invention to reduce cardiotoxicity associated with free doxorubicin therapy in the treatment of liver cancer.

It is an object of this invention to provide enhanced anti-tumor activity of conventional cancer therapies, including improved pharmacokinetics and biodistribution.

It is an object of this invention to provide compositions and methods that are minimally immunogenic when administered in vivo.

The preceding objectives are achieved by providing compositions for the targeted delivery of a therapeutic agent to a tissue expressing asialoglycoprotein receptors. The compositions contain an effective amount of the agent encapsulated in a liposome coupled to a desialyated glycoprotein, e.g., desialyated glycoprotein-$\alpha 1$.

This invention further provides methods for the targeted delivery of a therapeutic agent to a tissue expressing asialoglycoprotein receptors by delivery to the tissue an effective amount of a composition containing an effective amount of the agent encapsulated in a liposome coupled to a desialyated glycoprotein, e.g., desialyated glycoprotein-$\alpha 1$.

Also provided by this invention is a method for inhibiting the proliferation of liver cancer by administering to a subject in need of such therapy an effective amount of a composition containing doxorubicin encapsulated in desialyated glycoprotein-$\alpha 1$ coupled to a liposome.

MODES FOR CARRYNG OUT THE INVENTION

The practice of the present invention employs, unless otherwise indicated, conventional techniques of molecular biology (including recombinant techniques), microbiology, cell biology, biochemistry and immunology, which are within the skill of the art. Such techniques are explained fully in the literature. Such techniques are explained fully in the literature, such as, "Molecular Cloning: A Laboratory Manual," second edition (Sambrook et al., 1989); "Oligonucleotide Synthesis" (M. J. Gait, ed., 1984); "Animal Cell Culture" (R. I. Freshney, ed., 1987); the series "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987, and periodic updates); "PCR: The Polymerase Chain Reaction," (Mullis et al., eds., 1994); "Current Protocols in Immunology" (J. E. Coligan et al., eds., 1991).

Definitions

As used herein, certain terms may have the following defined meanings.

As used in the specification and claims, the singular form "a," "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "subject" or "host" is a vertebrate, preferably an animal or mammal, more preferably a rat, mouse, monkey, ape or a human patient. Mammals include, but are not limited to, murines, simians, human patients, farm animals, sport animals, and pets.

The terms "cancer," "neoplasm," and "tumor," used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by such procedures as CAT scan, magnetic resonance imaging (MRI), X-ray, ultrasound or palpation. Biochemical or immunologic findings alone may be insufficient to meet this definition.

As used herein, "inhibit" means to delay or slow the growth, proliferation or cell division of cells.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin REMINGTON'S PHARM. SCI., 15th Ed. (Mack Publ. Co., Easton (1975)).

An "effective amount" is an amount sufficient to effect beneficial or desired results. For example, a therapeutic amount achieves the desired therapeutic effect. This amount may be the same or different from a prophylatically effective amount that will prevent onset of disease or disease symptoms. An effective amount can be administered in one or more administrations, applications or dosages.

Doxorubicin (dox) is an anthracycline antibiotic originally derived from the fungus *Streptomyces peucetius* [1]. It has been found to be effective against a wide range of human malignant neoplasm, including acute leukemia, breast cancer and Hodgkin's disease. Doxorubicin exerts its anti-tumor effect via enzymatic reductions by for example NADPH cytochrome P450 reductase to yield active quinone intermediates that inhibit mitochondrial oxidative phosphorylation [2, 3], DNA repair enzymes [4] and topoisomerase I [5]. However, in well-oxygenated tissues such as the heart, the quinone intermediates enter redox cycling and produce highly reactive free radicals, which can cause oxidative damage to nearby and distant biomolecules. A major handicap of doxorubin therapy is in fact cardiotoxicity in the form of cardiomyopathy leading to congestive heart failure [6].

This invention provides a composition for the targeted delivery of a therapeutic agent to a tissue expressing asialoglycoprotein receptors. The compositions comprise an effective amount of the agent encapsulated in a liposome coupled to desialyated glycoprotein, e.g., desialyated glycoprotein-α1. In one embodiment, the therapeutic agent is a drug or a polynucleotide, e.g., cDNA encoding a therapeutic protein, a ribozyme, and antisense DNA or a cytotoxic drug, or a protein. When the therapeutic agent is cDNA, the liposome in preferably modified to incorporate cationic lipids such as 1,2, dioleoyl-3-trimethylammonium propane ("DOTAP") using methods well known in the art [23, 24]. Examples of cytotoxic drugs include, but are not limited to doxorubicin, vincristine, daunorubicin, and amphiphatic amines as described in [25, 26]. In one aspect, the liposome is couples to desialyated glycoprotein-α1 by an avidin-biotin or a thiol-maleamide linkage using methods well known in the art [27, 28].

This invention also provides a method for targeted delivery of therapeutic agent to a tissue expressing asialoglycoprotein receptors by delivering to the tissue an effective amount of the composition of the invention described herein. The method can be practiced in vitro, ex vivo or in vivo. When practiced in vitro, the method provides a simple assay or screen to determine the effectiveness of the drug delivery or therapeutic agent for achieving the desired therapeutic or prophylactic effect. The cells can be isolated and cultured from a biopsy or can be from a cultured cell line. The method can be further modified for incorporation into a high through-put screen.

In vivo practice of the invention in an animal such as a rat or mouse provides a convenient animal model system that can be used prior to clinical testing of the therapeutic agent.

When practiced in vivo, the composition is administered to the animal in effective amounts. As used herein, the term "administering" or "delivering" for in vivo and ex vivo purposes (if the target cell population is to be returned to the same (autologous) or another patient (allogeneic)) means providing the subject with an effective amount of the composition to achieve the desired therapeutic effect. In these instances, the composition may be administered with a pharmaceutically acceptable carrier. The compositions of the present invention can be used in the manufacture of medicaments and for the treatment of humans and other animals by administration in accordance with conventional procedures, such as an active ingredient in pharmaceutical compositions.

Methods of administering pharmaceutical compositions are well known to those of ordinary skill in the art and include, but are not limited to, microinjection, intravenous or parenteral administration. The compositions are intended for local administration as well as intravenously, subcutaneously, or intramuscularly. Administration can be effected continuously or intermittently throughout the course of the treatment. Methods of determining the most effective means and dosage of administration are well known to those of skill in the art and will vary with the agent used for therapy, the purpose of the therapy, and the subject being treated. Single or multiple administrations can be carried out with the dose level and pattern being selected by the treating physician.

The compositions also can be administered to subjects or individuals susceptible to or at risk of developing disease. In these embodiments, a "prophylactically effective amount" of the composition is administered to maintain homeostasis.

In vivo and ex vivo, the method also provides a means to deliver a therapeutic agent to a cell or tissue of interest. For example, the method is useful to inhibit the proliferation of liver cancer by administering to a subject in need of such therapy an effective amount of a composition containing doxorubicin encapsulated in a composition comprising a liposome coupled to a desialyated glycoprotein-α1.

The following examples are intended to illustrate, but not limit the inventions described herein.

EXPERIMENTAL EXAMPLES

Materials and Methods

Materials

L-α-phosphatidylcholine (PC), cholesterol (Chol), α1 acid-glycoprotein, doxorubicin hydrochloride (dox), N-hydroxysuccinimido-biotin (NHSB) and neuraminidase were purchased from Sigma Chemical Co. (St. Louis, Mo.). Avidin and dipalmityl phosphatidylserine (PS) were obtained from CalBiochem (San Diego, Calif.). RPMI 1640 medium, bovine calf serum, penicillin and streptomycin were purchased from Gibco Life Technologies (Grand Island, N.Y.).

Cell Culture

Human hepatoblastoma cells (HepG2) were obtained from American Tissue Cell Culture (Rockville, Md.) and maintained in RPM 1640 medium supplemented with 5% fetal calf serum, 100 units/ml penicillin and 100 µg/ml streptomycin in an incubator with a humidified, 5% $CO_2$ atmosphere cells were seeded at a density of $1\times10^4$ cells/well in 96-well plates or $1\times10^5$ cells/well in 24-well plates and incubated for 18–22 h prior to treatment.

Animals

Inbred nu/nu BALB/c nude mice aged 6–8 weeks were Laboratory Animal Service Center of the Chinese University of Hong Kong pathogen-free conditions. They were fed with standard animal diet (PICO LAB® Rodent Diet) and tap water ad libitum and kept in autoclaved cages with polyester fiber filters. All their diet and water were also autoclaved before use.

Liposome Preparation

Liposomes were prepared by thin film hydration [16]. Briefly, lipids in a molar PC:Chol:PS ratio of 11:4:0.025 were dissolved in chloroform and the chlorophyll was allowed to evaporate under nitrogen and the film further dehydrated under vacuum for 3–4 h. The lipids were then hydrated with 300 mM citrate buffer (pH 4). After 5 freeze and thaw cycles, the resulting multilamellar vesicles were extruded through 100 nm pore size polycarbonate membranes (Lipofast™, Avestin Inc., Ottawa, ON) to obtain unilamellar liposomes.

Encapsulation

For encapsulation of dox, a pH gradient was established by in raising the pH of the external medium to pH 7.5 using a 500 mM sodium carbonate buffer. The liposomes were heated for 5 min at 60° C. before addition of dox at a lipids:dox ratio of 20:1 (w:w) and heated for a further 10 min. Encapsulation efficiency was about 95% using this method [16]. Liposomal dox could be separated from free dox by exclusion chromatography using a Sephadex G50 column. Dox content of the liposomes was determined spectrophotometrically at 480 nm dissolved in acidified isopropanol (0.075M HCl in 90% isopropanol).

Coupling

Coupling of α1 acid-glycoprotein, desialyated by neuraminidas digestion, to liposome was achieved by forming avidin-biotin bridges: liposomes and protein were separately biotinylated by using NHSB, and coupled by the addition of avidin in the molar liposome (PS):protein:avidin ration of 1:1:1.

In Vitro Studies

Cytotoxicity Assay

HepG2 cells seeded in 96-well plates were incubated with 5 μM equivalents of free dox (D), dox-liposome (DL) or dox-liposome coupled to desialo-α1 acid-glycoprotein (DLG) for 24 h at 37° C. Cytotoxicity was measured using the standard MTT assay.

Flow Cytometry Studies

HepG2 cells seeded in 24-well plates were incubated with 10 μM equivalents of D, DL or DLG for 2 h at 37° C. The cells were 1 hen washed and harvested. Samples were analysed for dox content using a FACSort flow cytometer (Becton Dickinson, San Jose, Calif.).

Results

The anti-tumor activity of the desialo-α1 acid-glycoprotein conjugated doxliposome (DLG) was initially examined in vitro using the HepG2 cells. The IC50 for free dox (D) on HepG2 was found to be 5 μM, and this concentrated was used to perform cytotoxicity measurements with DL and DLG. It was found that the cytotoxic effect of both DL and DLG were similar to that of dox (FIG. 1).

In Vivo Studies

Anti-Tumor Efficacy

Nude mice (body weight 20–25 g; 6–8 weeks) were inoculated subcutaneously (s.c.) with a suspension of HepG2 cells ($4\times10^6$/mouse) on Day 0. On Day 2, groups of five mice were injected intravenously with 1 mg/kg equivalents of D, DL or DLG. The Control group received injections of saline. Injections were carried out every other day. Tumor volume was continuously monitored using a Vernier caliper. Measurements were taken weekly and volumes were calculated according to the formula (L×W×H×0.52) [17]. All mice were sacrificed on Day 35, and the tumors were removed and weighed.

Tissue Distribution Studies

On Day 35, the four groups of mice were given an extra injection of saline, D, DL or DLG respectively, and sacrificed 2 h later. The liver heart and tumor were immediately removed and homogenized in 10 mM $Na_2HPO_4$, buffer (pH 7.2). For the determination of dox in the different tissue s 1 ml of the homogenate was added to 3 ml of chloroform/isopropanol (1:1 v/v ) and mixed thoroughly. After centrifugation (1200 g for 10 min), the concentration of dox in the organic layer was determined fluorometrically at an excitation wavelength of 480 nm and an emission wavelength of 580 nm.

Myocardial Injury

On Day 35, the mice were ether-anesthetized, heparinized and blood samples were obtained by cardiac puncture. Myocardial injury was assessed by measuring the plasma lactate dehydrogenase (LDH) activity [18] using an assay kit from Sigma.

Histological Studies

Heart taken from one mouse from each of the four groups was carefully removed and fixed in Bouin's fluid. After fixing, the heart was processed and sectioned prior to HE staining. The sections were observed and photographed using an Olympus light microscope.

Results and Discussion

Figure 2:
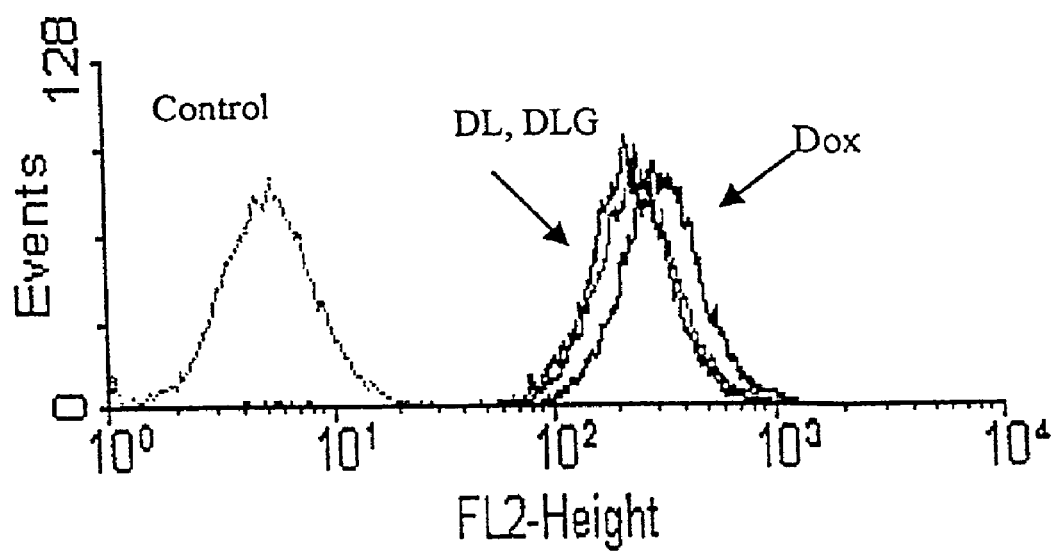
FIG. 2 shows uptake of doxorubicin by hepatoma cells. HepG2 cells were incubated with 20 μM equivalents of D, DL or DLG for 2 h at 37° C. After incubation, the medium was removed and the cells harvested. Cell samples were analyzed for dox content (FL2 Height) using a FACSort flow cytometer.

In order to ascertain whether the uptake of the liposomal formulations differed from that of the free drug, uptake was monitored using flow cytometry. FIG. 2 shows that instead of any increased uptake of encapsulated dox by the HepG2 cells, there was in fact a 30% decrease. There was no significant difference between DL and DLG.

Figure 3:
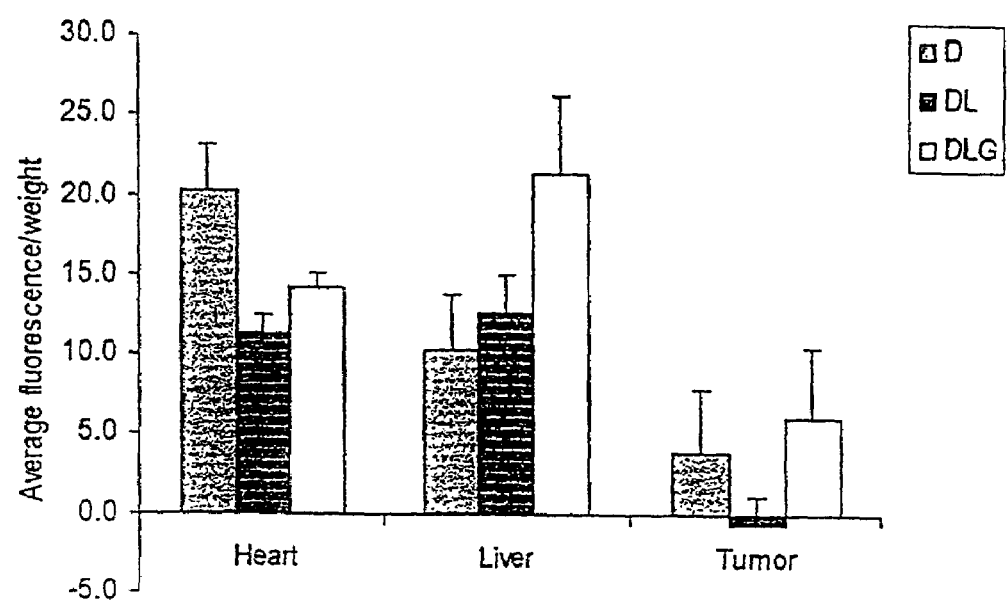
FIG. 3 shows tissue distribution of doxorubicin in nude mice. Nude mice were injected intravenously with 1 mg/kg dox equivalents of D, DL or DLG. The control group received injections of saline. The mice were sacrificed 2 h after injections. The organs were removed, weighted and homogenized. The concentration of dox in the homogenates was measured fluorimetrically ($\lambda_{ex}$=480 nm, $\lambda_{em}$=580 nm). Each column represents the mean ±s.d. (n=4).

The biodistribution of free and encapsulated dox is shown in FIG. 3. After 2 h post-injections, dox accumulation in the heart was reduced when dox was encapsulated in liposomes as compared to free dox. However, accumulation in the liver was similar in the dox and DL treated animals. Importantly, when the animals were injected with DLG, accumulation in the liver was more than 2-fold higher compared with free dox. Thus the desialo-α1 acid-glycoprotein exerted a targeting effect on dox delivery to liver cells. While dox content in the HepG2 tumors in the free dox and DLG-treated mice were similar it was lower in DL-treated mice. The higher liver content from DLG treatment relative to DL treatment showing a targeting function brought about by the desialo-α1 acid-glycoprotein.

Figure 4:
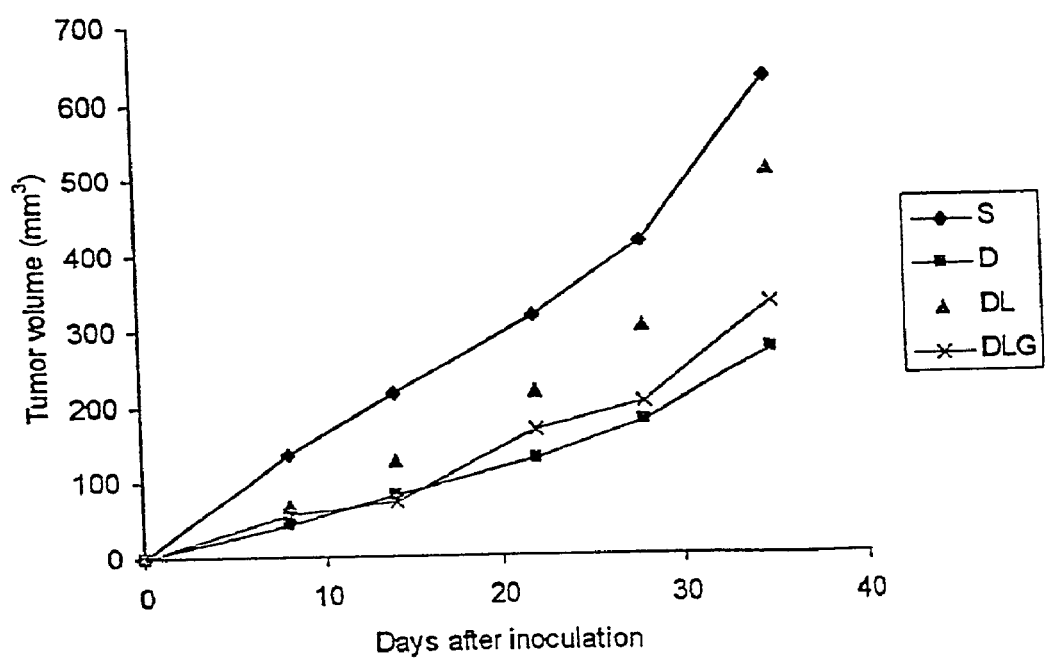
FIG. 4 shows the effect of doxorubicin on tumor volume in nude mice. Nude mice were inoculated s.c. with 4×10⁶ HepG2 cells on day 0. On day 2, groups of five mice were injected intravenously with 1 mg/kg dox equivalents of D, DL or DLG. The control group received injections of saline (S). Injections were carried out every other day. The tumor size was measured weekly and the volume calculated using the formula 0.52×L×W×H. Each point represents the mean volume from each group of 5 mice.

The dox content in the tumors also reflected the ability of the drug to suppress tumor growth. Thus DL was not effective in suppressing tumor growth (FIG. 4). In contrast, both D- and DLG-treatment of the mice resulted growth inhibition of about 40%. The anti-tumor ability of the DLG formulation was comparable to that of free dox, and greatly outperformed DL.

Figure 5:
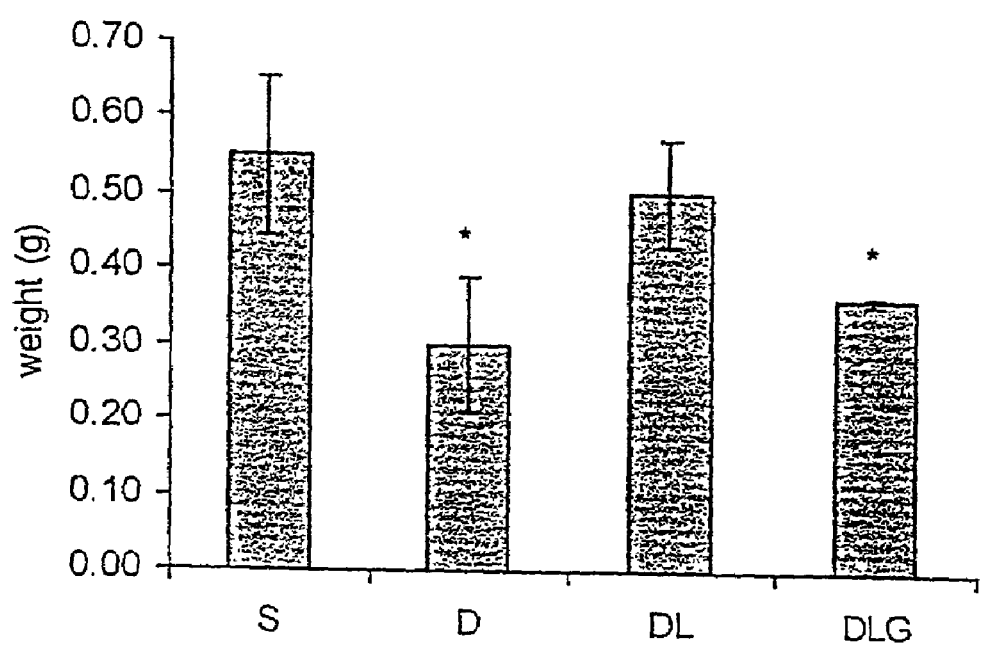
FIG. 5 shows the effect of doxorubicin on tumor weight in nude mice. Nude mice were inoculated s.c. with 4×10⁶ HepG2 cells on day 0. On day 2, groups of five mice were injected intravenously with 1 mg/kg dox equivalents of D, DL or DLG. The control group received injections of saline. Injections were carried out every other day. All mice were sacrificed on day 35. The tumors were removed and weighted. Each column represents the mean ±s.d. (n=5). *p<0.05 statistically significant difference as compared to control (student's t-test).
Figure 6:
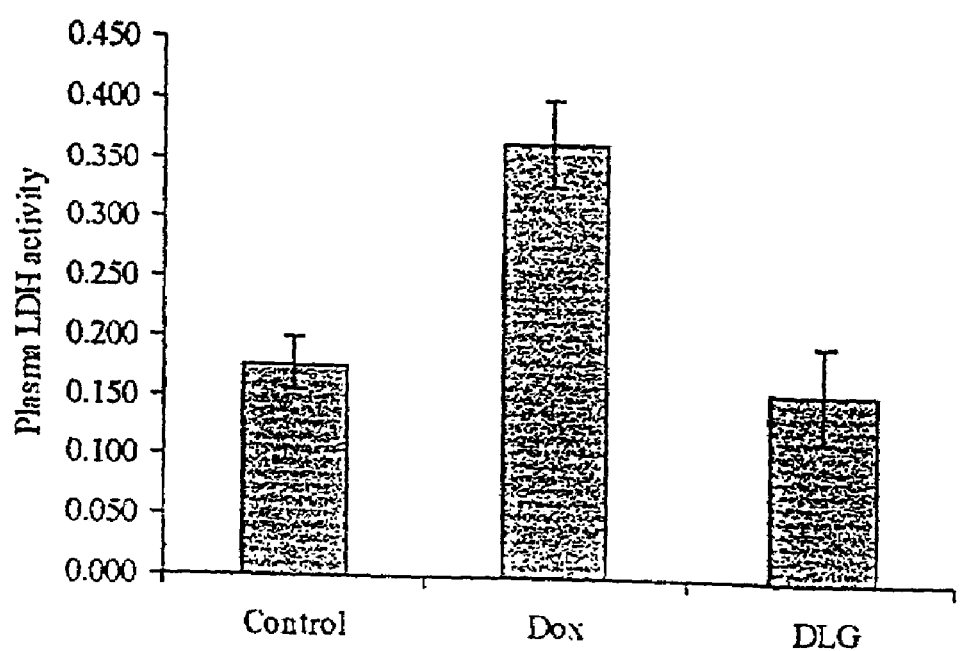
FIG. 6 shows the effect of doxorubicin on myocardial injury. Nude mice were inoculated s.c. with 4×10⁶ HepG2 cells on day 0. On day 2, groups of four mice were injected intravenously with 1 mg/kg dox equivalents of D or DLG. The control group received injections of saline. Injections were carried out every other day. On day 35, the mice were ether-anesthetized and heparinized blood samples were obtained by cardiac puncture. Myocardial injury was assessed by measuring the plasma lactate dehydrogenase (LDH) activity, using an assay kit from Sigma.
Figure 7:
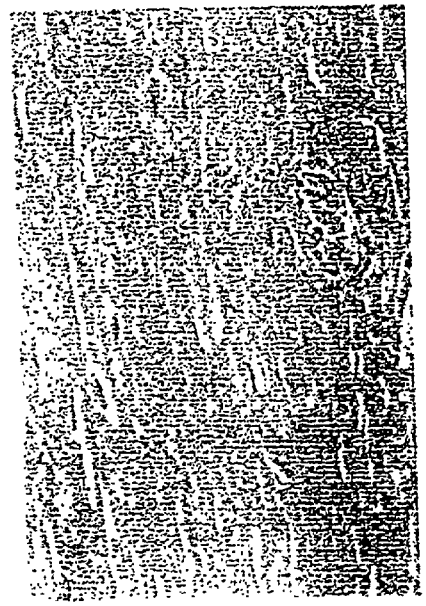
FIG. 7 shows the effect of doxorubicin on myocardial structure. Nude mice were inoculated s.c. with 4×10⁶ HepG2 cells on day 0. On day 2, the mice were injected intravenously with 1 mg/kg dox equivalents of D or DLG. The control group received injections of saline. Injections were carried out every other day. All mice were sacrificed on day 35. The heart was carefully removed and immediately fixed in Bouin's fluid. Heart sections were processed and stained with HE strain. The stained sections were observed using a light microscope and photographed. A-control; B-D-treated; C-DLG-treated.
Figure 7:
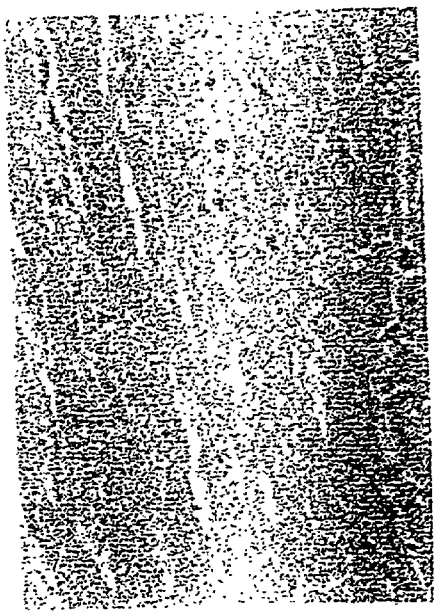
Figure 7:
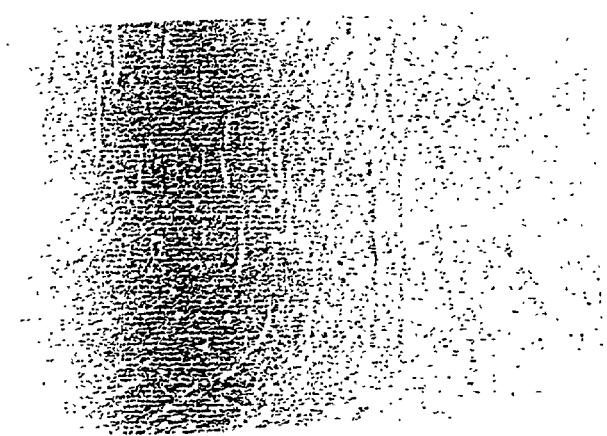

When the desialo-AαG targeted dox-liposome formulations were given in vivo to HepG2-tumor bearing nude mice, control dox-liposomes without any targeting protein ligand suppressed tumor growth only to a very small extent (FIG. 4). While liposomes are not very efficient drug carriers, they could improve the antitumor efficacy of dox in some systems [10]. Surprisingly, the anti-tumor activity of dox-liposomes was greatly enhanced when the liposomes were conjugated with desialo-AαG, such that the anti-tumor effect became comparable to that of free dox (FIG. 5). Since there was a pronounced reduction in the dox-induced injury to the heart when treatment was carried out with DLG instead of free dox, the therapeutic benefits of the targeted liposomal dox formulation in enhancing the therapeutic utility of this anti-tumor agent was considerable.

REFERENCES

1. Arcamone, F., et al. (1969) Biotechnol. Bioeng 11:1101–10.
2. Marcillat, O., et al. (1989) Biochem.J. 259:181–189.
3. Muammed, H., et al. (1992) Biochim. Biophys. Acta 722:43–50.
4. Bachur, N. R., et al. (1992) Mol. Pharmacol. 41:993–998.
5. Foglesong, P. D., et al. (1992) Cancer Chemother. Pharmacol 30:123–125.
6. Singal, P. K. et al. (1997) FASEB 11:931–936.
7. Gabizon, A. A. (1994) New Drug Therapy 8:431–450.

8. Gorden, D., et al. (1990) Biochim. Biophys. Acta 1029: 285–294.
9. Balazsovits, J. A. E., et al. (1989) Cancer Chemothrs. Pharmacol 23:81–86.
10. Gabizon, A., et al. (1982) Cancer Res. 42:4734–4739.
11. Longman, S. A., et al. (1995) 36:91–101.
12. Papahadjopoulos, D., et al. (1992) Proc. Natl. Acad. Sci USA 88:11460–11464.
13. Hwag, K. J. et al. (1980) Proc. Natl. Acad. Sci. USA 77:4030–403.
14. Baenzigesr, J. U. and Maynard, Y. (1980) J. Biol. Chem. 255:4607–4613.
15. Park, J. H., et al. (1998) Biochem. Biophys. Res. Commun. 244:304–311.
16. Mayer, L. D., et al. (1990) 1025:143–151.
17. Huang, S. K., et al. (1994) Cancer. Res. 54:2186–2191.
18. Li, P. C., et al. (1996) Am. J. Chin. Med. 24:255–262.
19. Webb, M. S., et al. (1998) Cancer Chemother. Pharmacol. 42:461–470.
20. Gregoriadis, G. ed. (1988) Liposomes as Drug Carriers (Wiley, N.Y.), 1863.
21. Allen, T. M., et al. (1989) Biochim. Biophys. Acta 981:27–35.
22. Matthay, K. K., et al. (1984) Cancer Res. 44:1880–1886.
23. Pedroso de Limar, M. et al. (1999) Mol. Membrance Biol. 16:103–109.
24. Kawakami, S., et al. (1998) Biochem. Biophys. Res. Commun. 252:78–83.
25. Mayer, L.D., et al. (1990) Cancer Res. 50:575–579.
26. Forssen, E. A., et al. (1992) Cancer Res. 52:3255–3261.
27. Pagnan, G., et al. (2000) J. Natl. Cancer Inst. 92:253–261.
28. Suzuki, S., et al. (1997) Brit. J. Cancer 76:83–89.

What is claimed is:

1. A composition for the targeted delivery of an active agent to a tissue expressing asialoglycoprotein receptors comprising said agent encapsulated in a liposome having a molar ratio PC:Chol:PS of 11:4:0.025 coupled to desialyated glycoprotein-α1.

2. The composition of claim 1, wherein the agent is a drug or polynucleotide.

3. The composition of claim 2, wherein the polynucleotide is cDNA encoding a protein, a ribozyme, or antisense DNA.

4. The composition of claim 1, wherein the agent is selected from the group consisting of cytotoxic drugs and proteins.

5. The composition of claim 4, wherein the cytotoxic drug is selected from the group consisting of doxorubicin, vincristine, daunorubicin, and amphipathic amines.

6. The composition of claim 1, wherein the desialyated glycoprotein-α1 is coupled to the liposome by an avidin-biotin or thiol-maleamide linkage.

7. A method for targeted delivery of an active agent to a tissue expressing asialoglycoprotein receptors comprising delivering to the tissue the composition of claim 1 or 6.

8. A composition for the targeted delivery of an active agent to a tissue expressing asialoglycoprotein receptors comprising doxorubicin encapsulated in a liposome having a molar ratio PC:Chol:PS of 11:4:0.025 coupled to desialyated glycoprotein-α1 by an avidin-biotin linkage.

9. A method for targeted delivery of an active agent to a tissue expressing asialoglycoprotein receptors comprising delivering to the tissue the composition of claim 1, whereby the agent is a polynucleotide or protein.

10. A method for targeted delivery of an active agent to a tissue expressing asialoglycoprotein receptors comprising delivering to the tissue the composition of claim 2, whereby the polynucleotide is cDNA encoding a protein, a ribozyme, or antisense DNA.

11. A method for targeted delivery of an active agent to a tissue expressing asialoglycoprotein receptors comprising delivering to the tissue the composition of claim 1, whereby the agent is selected from the group consisting of doxorubicin, vincristine, daunorubicin, and amphipathic amines.

* * * * *